United States Patent [19]

Kring et al.

[11] 4,235,097

[45] Nov. 25, 1980

[54] DOSIMETER FOR MEASURING GASEOUS CONTAMINANTS

[75] Inventors: Elbert V. Kring, Wilmington, Del.; William J. Lautenberger, Philadelphia, Pa.

[73] Assignee: E. I. Du Pont de Nemours and Company, Wilmington, Del.

[21] Appl. No.: 24,386

[22] Filed: Mar. 27, 1979

[51] Int. Cl.³ ............................................. G01N 31/06
[52] U.S. Cl. ............................................. 73/23; 422/88
[58] Field of Search ............................... 73/23; 422/88

[56] References Cited

U.S. PATENT DOCUMENTS

| 3,924,219 | 12/1975 | Braun | 73/23X |
|---|---|---|---|
| 3,950,980 | 4/1976 | Braun et al. | 73/23 |
| 3,985,017 | 10/1976 | Goldsmith | 73/23 |
| 4,040,805 | 8/1977 | Nelms et al. | 73/23 X |
| 4,132,616 | 1/1979 | Tantram et al. | 204/195 P |

OTHER PUBLICATIONS

Palmes, E. D., et al. *Personal Sampler for Nitrogen Dioxide,* in Am. Ind. Hyg. Assoc. J., vol. 37, pp. 570–577, Oct. 1976.

*Primary Examiner*—Gerald Goldberg
*Assistant Examiner*—Joseph W. Roskos

[57] ABSTRACT

A personal dosimeter for measuring the time-average concentration of a gaseous contaminant in the atmosphere in a manner substantially independent of atmospheric motion relative to the dosimeter is provided. The dosimeter comprises a detector substance capable of chemically or physically combining with the gaseous contaminant disposed tightly between two substantially flat members, at least one of which has a plurality of through-and-through channels. The members have corresponding, meshing shapes such that the channels provide the only communication between the atmosphere and the detector substance, allowing the gaseous contaminant to diffuse through the channels.

5 Claims, 4 Drawing Figures

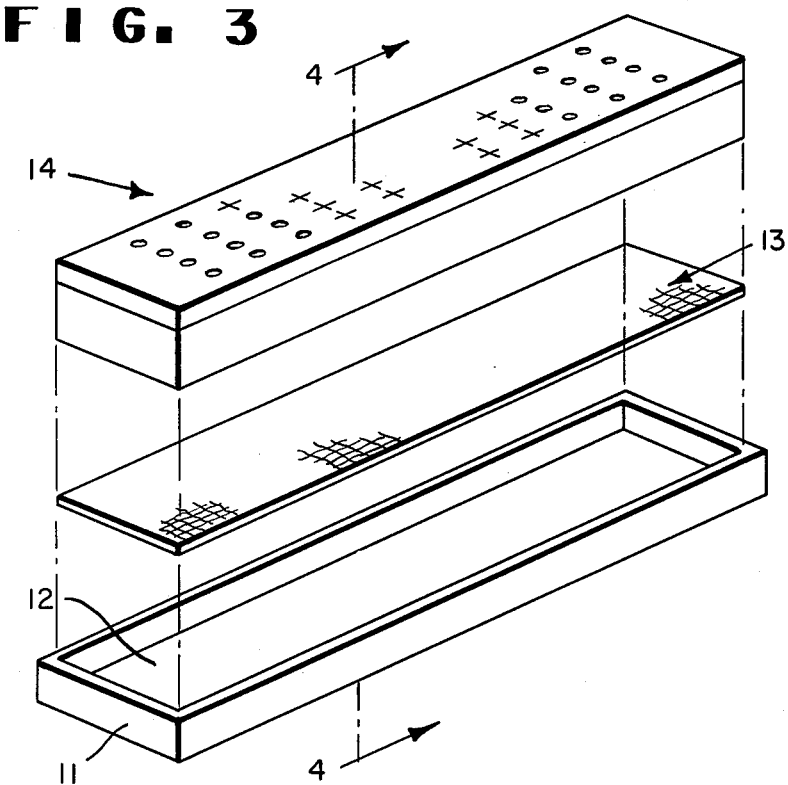
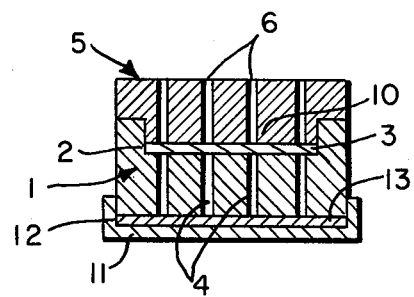

DOSIMETER FOR MEASURING GASEOUS CONTAMINANTS

BACKGROUND OF THE INVENTION

1. Field Of The Invention

This invention is related to a personal dosimeter for registering gaseous contaminants in the atmosphere. More particularly, it is related to an integrating dosimeter useful in measuring the average exposure level to a gaseous contaminant over a given period of time.

1. Description Of The Prior Art

Monitoring of pollutants in the air is increasingly important as the harmful effects of such pollutants become evident. In large work-places, for example, one device for this purpose has used a pump which forces the air to be sampled in a continuous, uniform stream over a sensing element. Such devices do not, however, accurately monitor the exposure of a moving individual within the large area being sampled.

Personal sampling devices which are worn by individual workers and which passively collect the contaminants have also been used. Devices which employ the molecular diffusion of the monitored gaseous contaminant to collect the sample have been shown, for example, in U.S. Pat. Nos. 3,924,219 and 3,985,017. Many devices which allow the gaseous contaminant to diffuse to a collecting medium can give inaccurate indications of average contaminant concentration because the devices collect varying amounts of contaminant, being adversely affected by atmospheric circulation patterns or motion of the individual wearing the device.

The solution to this problem employed in prior art devices, which has essentially involved restricting the diffusion rate, has often made the device somewhat insensitive to low concentrations of the gaseous contaminants. Therefore, there remains a need for a dosimeter which is independent of relative atmospheric motion and which operates satisfactorily at low contaminant concentrations.

SUMMARY OF THE INVENTION

According to the present invention, there is provided a personal dosimeter for measuring the average concentration of a gaseous contaminant in the atmosphere over a given period of time. The dosimeter comprises a flat base having a shallow cavity therein;

a detector substance capable of interacting with the gaseous contaminant situated within the cavity; and a cover sheet, overlaying the base, the interior side of which meshes with the cavity in the base such that the detector substance is enclosed and disposed tightly between the cavity bed and the cover sheet, wherein at least one of the base and the cover sheet has a plurality of through-and-through circular channels, each channel having a length-to-diameter ratio of at least 3, such that the channels provide the only communication between the atmosphere and the detector substance.

BRIEF DESCRIPTION OF THE DRAWINGS

FIG. 3 is a partially exploded view of another embodiment of the invention showing the assembled device of FIG. 1 combined with a second detector substance.

FIG. 4 is a cross-sectional view of the dosimeter of FIG. 4, fully assembled, taken along line 4—4.

DETAILED DESCRIPTION OF THE INVENTION

The dosimeter described herein collects, for subsequent analysis, a gaseous contaminant in proportion to its average concentration in the atmosphere during the collection period. The dosimeter passively samples the gaseous contaminant by allowing diffusion of the contaminant through a plurality of channels into an interior portion of the dosimeter where it is maintained by a detector substance until it is analyzed.

The operation of the dosimeter is based on Fick's Law which gives a mathematical expression for the molecular diffusion, or transfer, of a gaseous contaminant in the air through a channel. In relevant form, it is expressed as $$M = D \cdot C \cdot t \cdot A / L$$

where $M$ = quantity of gaseous contaminant transferred (mg)

$D$ = diffusion coefficient of the gaseous contaminant through air (cm$^2$/min)

$C$ = concentration of the contaminant in the atmosphere (mg/cm$^3$)

$t$ = time of exposure (minutes)

$A$ = cross-sectional area of the channel (cm$^2$)

$L$ = distance in direction of diffusion, herein channel length (cm)

Values of $D$ for various gaseous contaminants are readily obtainable from the literature. Fick's Law applies to each channel in the dosimeter.

Figure 1:
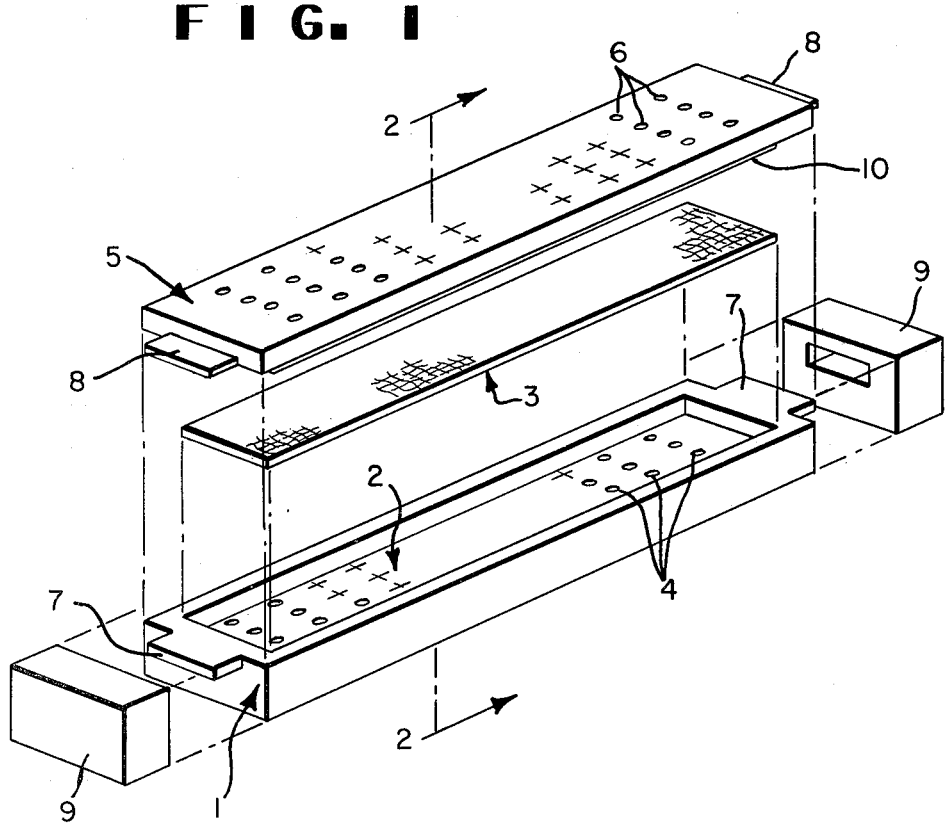
FIG. 1 is an exploded view of a dosimeter in which both the base and cover sheet contain diffusion channels.
Figure 2:
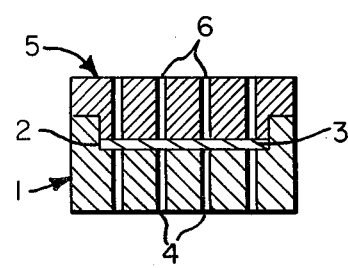
FIG. 2 is a cross-sectional view of the dosimeter of FIG. 1, in assembled form, taken along line 2—2.

With respect to FIGS. 1 and 2, there is shown a dosimeter comprising a base 1 having a shallow cavity 2 in which is disposed a layer of a detector substance 3 which completely covers the flat bed of cavity 2.

A cover sheet 5, corresponding in length and width to base 1, has a protruding portion 10 which tightly meshes in a friction-fit with the walls of cavity 2 as shown in FIG. 2. When cover sheet 5 and base 1 are fit together, detector substance 3 is set tightly between protrusion 10 and the bed of cavity 2, leaving no space between the detector substance and either the cavity bed or the protrusion. The desired tight fit is aided by providing base 1 with flanges 7 which correspond to flanges 8 provided to cover sheet 5. Each pair of flanges 7 and 8 is clamped together by inserting it into the corresponding slot of one of end-caps 9 as shown.

Cover sheet 5 has a plurality of circular channels 6 extending from its top, exterior face through protrusion 10. Base 1 also has a plurality of circular channels 4 extending from the bed of cavity 2 through the opposite side of base 1. When cover sheet 5 and base 1 are fit together, enclosing detector substance 3, channels 4 and 6 provide the only communications between the atmosphere and detector substance 3.

When the dosimeter is in operation, the gaseous contaminant diffuses through channels 4 and 6 according to Fick's Law and is maintained by detector substance 3 until analysis is to be made. The detector substance can be any material that absorbs, adsorbs, reacts, or otherwise combines with the gaseous contaminant. Regardless, of the manner in which the detector substance interacts, as above, with the gaseous contaminant, its quantity or strength should be sufficient to completely interact with the total quantity of contaminant which it contacts. The detector substance will often be specific to the particular gaseous contaminant being monitored. Examples of detectors useful for various contaminants are activated carbon or charcoal, silica gels, porous polymers, and activated alumina. The carbon or alumina, for example, can be embedded in a polymeric binder such as polytetrafluoroethylene.

Cover sheet 5 and base 1 are preferably made from materials that are nonhygroscopic and both chemically and physically inert to the gaseous contaminant being monitored. Examples of such materials are polyethylene, polypropylene, polymers or copolymers of tetrafluoroethylene and hexafluoropropylene, stainless steel, and various metals. The above-named polymers are preferred since they can be easily injection-molded.

For a personal dosimeter to give an accurate indication of the time-average concentration of a gaseous contaminant in the atmosphere, it should be unaffected by air movement relative to the dosimeter, and should be sufficiently sensitive to collect adequate mass even at low concentrations. In the dosimeter of the present invention, collection of the gaseous contaminant is made through the channels whose ends lead directly into the detector substance, leaving no air space about the detector. It has been found that with such a configuration, when the channels have a length-to-diameter ratio of at least 2.5, preferably at least 3.0, and most preferably at least 3.4, the dosimeter is substantially independent of ambient velocity effects. Although the cross-section of the channels is normally round, it is to be understood that channels of other cross-sections would be operable. In such cases, the above length-to-diameter ratios (L/d) for circular cross-section can be converted to length-to-area ratios to develop a correspondence for other cross-sectional configurtions.

Within the constraints of the above ratios, any lengths or diameters, in circular channels for example, can be used, although an upper limit of about 10 is useful for L/d. Channel lengths in the range of approximately 0.1 to 1.0 cm. are preferred, as are diameters of about 0.04 to 0.25 cm. The desired size of the dosimeter, however, will generally determine the practical upper limits of the channel dimensions.

As can be seen from Fick's Law, the number of channels affects the quantity of gaseous contaminant collected since it affects the total cross-sectional area available for transfer. The dosimeter has commercially-acceptable sensitivity to low concentration with as few as 50 channels, however.

Although FIGS. 1 and 2 show channels in both cover sheet 5 and base 1, it is to be understood that the dosimeter performs equivalently when the channels are contained in only one or the other of these. Also, it is not necessary, when both do contain channels, that each contain the same number. Preferably, however, there are 200–350 channels, more preferably 275–325 channels, in each of the cover sheet and base.

In use, a dosimeter as described above is worn by the person exposed to the gaseous contaminant, usually by attaching the dosimeter to the clothing such that the channels are unobstructed. Alternatively, the dosimeter can be placed in a position when it will be exposed to an ambient air sample representative of the air to which the subject person is exposed. After the exposure for a measured period of time, the detector substance is analyzed for content of the gaseous contaminant. Values for levels of gaseous contaminant present can be mathematically related to ambient concentration by application of Fick's Law, giving the average ambient concentration during the exposure period.

Analysis can be accomplished by removing the detector substance and then applying standard analytically techniques to measure changes in the thermal, chemical or physical properties of the detector substance. Gas chromatography is a preferred analytical method. When it is desired to isolate the gaseous contaminant from the detector substance, such common desorption solvents as carbon disulfide, methylene chloride, ethers, and alcohols can first be used to strip the contaminant from the detector.

FIGS. 3 and 4 show a different embodiment of the present invention in which the dosimeter of FIGS. 1 and 2 (numbers 1–6 and 10 are as described with respect to FIGS. 1 and 2) is further combined with a system to detect break-downs in the collection operation of the detector substance.

With respect to FIGS. 3 and 4, dosimeter 14, which is the assembled device of FIGS. 1 and 2 minus flanges 7 and 8 and end-caps 9, is friction-fit into trough 12 of substrate 11. Disposed in trough 12 is a layer of detector substance 13 which completely covers the flat bed of trough 12. When dosimeter 14 is fit into trough 12, in an air-tight coupling, detector substance 13 is set tightly between base 1 and the bed of trough 12 bearing no space between the detector substance and either the trough bed or base 1. The size of trough 12 corresponds in length and width to that of base 1.

When the device of FIGS. 3 and 4 is in operation, the gaseous contaminant in the atmosphere diffuses to detector layer 3 only through channels 6 and can reach detector layer 13 only by diffusion through channels 4, which occurs only when there is a break-down in the collection by detector substance 3. Such a break-down occurs, for example, when detector substance 3 becomes saturated with gaseous contaminant. Detector substance 13 is normally the same material as detector substance 3.

By examining detector substance 13 for the presence of the gaseous contaminant, it can be determined whether saturation of detector substance 3 has occurred. A true measurement of the average concentration of the gaseous contaminant cannot be made when the detector substance becomes saturated before the end of the exposure period. In general, if detector substance 13 contains more than 15 parts by weight of contaminant per 100 parts by weight of pure detector substance 3, determinations based on amounts collected by detector 3 might be inaccurate.

Further considerations in determining the accuracy of contaminant-collection by a detector substance are given in Melcher, Langner, and Kagel, "Criteria for the Evaluation of Methods for the Collection of Organic Pollutants in Air using Solid Sorbents", *American Industrial Hygiene Association Journal*, Volume 39, page 349, May 1978.

Demonstration of the independence of the dosimeter to the relative movement of the atmosphere can be made by comparing experimental results of the dosimeter's operation under various conditions with theoretical values predicted from Fick's Law. The Fick equation previously described can be re-written as $$D \cdot A / L = M / (C \cdot t)$$

where each symbol has its afore-mentioned meaning. Since A and L are constants in any particular dosimeter and D, the diffusion coefficient, is independent of concentration (C), time (t), or mass collection (M), the mathematical expression D·A/L will be a constant for any particular dosimeter.

To illustrate, several dosimeters as in FIGS. 1 and 2 (wherein: (1) cover sheet 5 and base 1 each had 291 channels; (2) each channel had a diameter of 0.11 cm and a length of 0.352 cm; and (3) the detector substance was activated charcoal which was embedded in a matrix of polytetrafluoroethylene) were constructed. A total of three different tests was run, in each of which 2 dosimeters were placed in a chamber in which air having a known concentration of benzene was blown past the dosimeters in a direction parallel to the external faces of the base and cover sheet of each. The dosimeters were so exposed for 30 minutes, after which time the detector substance of each was removed, the collected benzene was desorbed with carbon disulfide, and the quantity of the benzene was determined with a previously-calibrated gas chromatograph. Results are tabulated below

| Test | C Benzene concentration (mg/cm$^3$ × 10$^5$) | Air Velocity (feet/min.) | t Exposure time (min.) | M Benzene Collected (mg × 10$^2$) | $\frac{M}{C \cdot t}$ (cm$^3$/min) |
|---|---|---|---|---|---|
| 1 | 11.4 | 32.5 | 30 | 31.9 | 93.4 |
|   | 11.4 | 32.5 | 30 | 28.6 | 83.8 |
| 2 | 2.14 | 162.5 | 30 | 5.7 | 88.8 |
|   | 2.14 | 162.5 | 30 | 5.49 | 85.8 |
| 3 | 1.024 | 325.0 | 30 | 2.99 | 97.3 |
|   | 1.024 | 325.0 | 30 | 2.85 | 92.8 |

The diffusion coefficient of benzene at the temperature of the test, approximately 23° C., is 5.592 cm$^2$/min (International Critical Tables). In these tests, the expression D·A/L has a value determined as $$D \cdot A/L = 5.592 \frac{\left[2 \times 291 \left(3.14 \left(\frac{0.11}{2}\right)^2\right)\right]}{0.352} = 87.8 \frac{cm^3}{min.}$$

The experimental results obtained for M/(C·t) are in substantial agreement with the theoretical value for D·A/L of 87.8 cm$^3$/min as predicted by the Fick equation.

In another demonstration of independence from relative atmospheric motion, 6 sets of 2 dosimeters each as in FIGS. 1 and 2, but having channels only in cover sheet 5, were constructed. The detector substance was activated charcoal which was embedded in a matrix of polytetrafluoroethylene. Each set differed from any other set in number of channels, channel length, or channel diameter. A dosimeter of each set was placed in a chamber in which air having a benzene concentration of 1.152 × 10$^{-5}$ mg/cm$^3$ was blown past in a direction parallel to the external face of the cover sheet of each. The velocity of the air relative to the dosimeter, was 5 ft./min. After 3 hours, the amount of benzene collected by each dosimeter was determined as described previously. The test was repeated with the remaining dosimeter except that a relative air velocity of 160 ft./min was employed.

For each set of dosimeters, the effect of the change in velocity was calculated as $$\text{Velocity Effect} = \frac{M_{160} - M_5}{M_5} \times 100\%$$

where
$M_{160}$ = Mass collected at 160 ft/min.
$M_5$ = Mass collected at 5 ft/min Results are tabulated below:

| Dosimeter Set | Number of Channels | L Channel Length (cm) | d Channel Diameter (cm.) | $\frac{L}{d}$ | Velocity Effect |
|---|---|---|---|---|---|
| 1 | 96 | 0.60 | 0.20 | 3.0 | 0.0% |
| 2 | 177 | 0.48 | 0.14 | 3.43 | −1.6% |
| 3 | 401 | 0.32 | 0.08 | 4.0 | +1.9% |
| 4 | 401 | 0.635 | 0.08 | 7.94 | −1.4% |
| 5 | 177 | 0.32 | 0.14 | 2.29 | +18.8% |
| 6 | 1 | 0.97 | 3.15 | 0.31 | +313.0% |

As can be seen, those dosimeters within the scope of the present invention—that is, dosimeters 1-4, wherein L/d ≧ 2.5—show negligible change in mass collection from change in ambient velocity. Control dosimeters 5 and 6, which are outside the present invention, show a substantial change. Dosimeter 6 demonstrates the extreme effects of ambient velocity when L/d is far less than the lower limit of the present invention.

What is claimed is:

1. A personal dosimeter for measuring the time-average concentration of a gaseous contaminant in the atmosphere comprising
    a flat base having a shallow cavity therein;
    a detector substance capable of interacting with the gaseous contaminant situated within the cavity; and
    a cover sheet, overlaying the base, the interior side of which meshes with the cavity in the base such that the detector substance is enclosed and disposed tightly between the cavity bed and the cover sheet, wherein at least one of the base and the cover sheet has a plurality of through-and-through circular channels, each channel having a length-to-diameter ratio of at least 3, and wherein the channels provide the only communication between the atmosphere and the detector substance.

2. The dosimeter of claim 1 in which the channels have a length of approximately 0.1-1.0 cm. and a diameter of approximately 0.04-0.25 cm.

3. The dosimeter of claim 2 wherein each of the cover sheet and the base has 200-350 channels.

4. The dosimeter of claim 1, 2, or 3 in which the detector substance is selected from the group consisting of activated charcoal, activated carbon, silica gels, activated alumina, and porous polymers.

5. A personal dosimeter for measuring the time-average concentration of a gaseous contaminant in the atmosphere comprising
    a flat substrate having a shallow trough therein;
    a first detector substance capable of interacting with the gaseous contaminant situated within the trough;
    a flat base having a shallow cavity in one side thereof, the base being fit within the trough such that the first detector substance is enclosed and tightly disposed between the trough bed and the side of the flat base opposite the shallow cavity;

a second detector substance capable of interacting with the gaseous contaminant situated with the cavity; and a cover sheet, overlaying the base, the interior side of which meshes with the cavity in the base such that the second detector substance is enclosed and disposed tightly between the cavity bed and the cover sheet, wherein each of the cover sheet and the base has a plurality of through-and-through circular channels, each channel having a length-to-diameter ratio of at least 3, wherein the channels in the base provide the only communication between the first and second detector substances, and wherein the channels in the cover sheet provide the only communication between the atmosphere and the second detector substance.

* * * * *